(12) United States Patent
Hestad

(10) Patent No.: US 9,770,266 B2
(45) Date of Patent: Sep. 26, 2017

(54) SPINAL CORRECTION TENSIONING SYSTEM

(71) Applicant: Zimmer Spine, Inc., Edina, MN (US)

(72) Inventor: Hugh D Hestad, Edina, MN (US)

(73) Assignee: Zimmer Spine, Inc., Edina, MN (US)

( * ) Notice: Subject to any disclaimer, the term of this patent is extended or adjusted under 35 U.S.C. 154(b) by 0 days.

(21) Appl. No.: 15/143,962

(22) Filed: May 2, 2016

(65) Prior Publication Data

US 2016/0242815 A1 Aug. 25, 2016

Related U.S. Application Data

(63) Continuation of application No. 14/495,297, filed on Sep. 24, 2014, now Pat. No. 9,339,299, which is a continuation of application No. 12/490,845, filed on Jun. 24, 2009, now Pat. No. 8,876,867.

(51) Int. Cl.
*A61B 17/70* (2006.01)

(52) U.S. Cl.
CPC ........ *A61B 17/7028* (2013.01); *A61B 17/702* (2013.01); *A61B 17/704* (2013.01); *A61B 17/7022* (2013.01); *A61B 17/7032* (2013.01); *A61B 17/7046* (2013.01)

(58) Field of Classification Search
CPC ................. A61B 17/7022; A61B 17/7028
See application file for complete search history.

(56) References Cited

U.S. PATENT DOCUMENTS

| 616,669 | A | | 12/1898 | Hoyt | |
|---|---|---|---|---|---|
| 4,041,939 | A | | 8/1977 | Hall | |
| 5,454,812 | A | * | 10/1995 | Lin | ................... A61B 17/7022 606/252 |

(Continued)

FOREIGN PATENT DOCUMENTS

| WO | WO-9505785 | 3/1995 |
|---|---|---|
| WO | WO-2006086537 A2 | 8/2006 |
| WO | WO-2010033567 | 3/2010 |

OTHER PUBLICATIONS

"European Application Serial No. 10251103.7, Communication Pursuant to Article 94(3) EPC dated Sep. 29, 2016", 4 pgs.

(Continued)

*Primary Examiner* — Ellen C Hammond
*Assistant Examiner* — Stuart S Bray
(74) *Attorney, Agent, or Firm* — Schwegman Lundberg & Woessner, P.A.

(57) ABSTRACT

A vertebral column correction system for correcting a spinal deformity without fusing the joint segments is disclosed. The vertebral column correction system may have first and second vertebral anchors secured to first and second vertebrae. The vertebral column correction system may further comprise one or more intermediate vertebral anchors secured to vertebrae between the first and second vertebrae. A connection member may be disposed within a head portion of the vertebral anchors. At least a portion of the connection member may be a flexible member, such as a flexible cord, configured for tensioning between at least two vertebral anchors for providing a desired amount of tension to apply a correctional force to the spinal column. A spring member, or other tensioning member, may maintain the tension of the connection member.

19 Claims, 9 Drawing Sheets

(56) References Cited

U.S. PATENT DOCUMENTS

| | | | |
|---|---|---|---|
| 5,725,582 A * | 3/1998 | Bevan | A61B 17/7022 24/129 W |
| 5,733,284 A * | 3/1998 | Martin | A61B 17/025 606/248 |
| 6,248,106 B1 | 6/2001 | Ferree | |
| 6,290,700 B1 | 9/2001 | Schmotzer | |
| 6,296,643 B1 | 10/2001 | Hopf et al. | |
| 6,299,613 B1 | 10/2001 | Ogilvie et al. | |
| 6,551,320 B2 | 4/2003 | Lieberman | |
| 6,623,484 B2 | 9/2003 | Betz et al. | |
| 6,652,526 B1 | 11/2003 | Arafiles | |
| 6,676,661 B1 | 1/2004 | Martin Benlloch et al. | |
| 6,986,771 B2 | 1/2006 | Paul et al. | |
| 6,989,011 B2 | 1/2006 | Paul et al. | |
| 7,029,475 B2 | 4/2006 | Panjabi | |
| 7,073,415 B2 | 7/2006 | Casutt et al. | |
| 7,137,985 B2 | 11/2006 | Jahng | |
| 7,326,210 B2 | 2/2008 | Jahng et al. | |
| 7,722,649 B2 | 5/2010 | Biedermann et al. | |
| 7,815,665 B2 | 10/2010 | Jahng et al. | |
| 7,854,752 B2 | 12/2010 | Colleran et al. | |
| 8,114,135 B2 | 2/2012 | Malandain | |
| 8,623,057 B2 | 1/2014 | Jahng et al. | |
| 8,641,734 B2 | 2/2014 | Moumene et al. | |
| 8,876,867 B2 | 11/2014 | Hestad | |
| 9,339,299 B2 | 5/2016 | Hestad | |
| 2002/0035366 A1 | 3/2002 | Walder et al. | |
| 2002/0040222 A1 * | 4/2002 | Hashimoto | A61B 17/7022 606/330 |
| 2002/0095151 A1 | 7/2002 | Dahla et al. | |
| 2002/0133155 A1 * | 9/2002 | Ferree | A61B 17/70 606/246 |
| 2002/0138077 A1 | 9/2002 | Ferree | |
| 2002/0193793 A1 * | 12/2002 | Kawakami | A61B 17/70 606/276 |
| 2003/0105459 A1 * | 6/2003 | Songer | A61B 17/0401 606/308 |
| 2004/0049190 A1 * | 3/2004 | Biedermann | A61B 17/7008 606/257 |
| 2004/0106921 A1 | 6/2004 | Cheung et al. | |
| 2004/1043264 | 7/2004 | McAfee | |
| 2004/0215191 A1 | 10/2004 | Kitchen | |
| 2004/0225289 A1 | 11/2004 | Biedermann et al. | |
| 2004/0236327 A1 | 11/2004 | Paul | |
| 2005/0010220 A1 | 1/2005 | Casutt et al. | |
| 2005/0056979 A1 | 3/2005 | Studer et al. | |
| 2005/0065514 A1 | 3/2005 | Studer | |
| 2005/0065516 A1 | 3/2005 | Jahng | |
| 2005/0085815 A1 | 4/2005 | Harms et al. | |
| 2005/0096652 A1 | 5/2005 | Burton | |
| 2005/0154390 A1 | 7/2005 | Biedermann et al. | |
| 2005/0177157 A1 | 8/2005 | Jahng | |
| 2005/0203513 A1 | 9/2005 | Jahng et al. | |
| 2005/0203514 A1 | 9/2005 | Jahng et al. | |
| 2005/0203517 A1 | 9/2005 | Jahng et al. | |
| 2005/0277922 A1 | 12/2005 | Trieu et al. | |
| 2006/0036240 A1 * | 2/2006 | Colleran | A61B 17/7025 606/86 A |
| 2006/0047282 A1 * | 3/2006 | Gordon | A61B 17/7016 606/86 A |
| 2006/0058792 A1 | 3/2006 | Hynes | |
| 2006/0142758 A1 | 6/2006 | Petit | |
| 2006/0195088 A1 | 8/2006 | Sacher et al. | |
| 2006/0195090 A1 | 8/2006 | Suddaby | |
| 2006/0212033 A1 | 9/2006 | Rothman et al. | |
| 2006/0247637 A1 * | 11/2006 | Colleran | A61B 17/7007 606/257 |
| 2007/0005062 A1 | 1/2007 | Lange et al. | |
| 2007/0005063 A1 | 1/2007 | Bruneau et al. | |
| 2007/0055244 A1 * | 3/2007 | Jackson | A61B 17/7028 606/86 A |
| 2007/0055245 A1 | 3/2007 | Sasso et al. | |
| 2007/0100341 A1 | 5/2007 | Reglos et al. | |
| 2007/0129729 A1 * | 6/2007 | Petit | A61B 17/7031 606/254 |
| 2007/0167948 A1 * | 7/2007 | Abdou | A61B 17/7005 606/86 A |
| 2007/0198088 A1 | 8/2007 | Biedermann et al. | |
| 2007/0233095 A1 | 10/2007 | Schlaepfer | |
| 2007/0270821 A1 | 11/2007 | Trieu et al. | |
| 2008/0033435 A1 * | 2/2008 | Studer | A61B 17/7028 606/256 |
| 2008/0033436 A1 | 2/2008 | Song et al. | |
| 2008/0125780 A1 * | 5/2008 | Ferree | A61B 17/0401 606/86 R |
| 2008/0140076 A1 * | 6/2008 | Jackson | A61B 17/7004 606/60 |
| 2008/0140122 A1 | 6/2008 | Bethell | |
| 2008/0140133 A1 * | 6/2008 | Allard | A61B 17/705 606/308 |
| 2008/0140202 A1 * | 6/2008 | Allard | A61B 17/7011 623/17.13 |
| 2008/0154307 A1 | 6/2008 | Colleran et al. | |
| 2008/0177316 A1 * | 7/2008 | Bergeron | A61B 17/7028 606/254 |
| 2008/0195153 A1 | 8/2008 | Thompson | |
| 2008/0234744 A1 * | 9/2008 | Zylber | A61B 17/7005 606/264 |
| 2008/0234747 A1 * | 9/2008 | Allard | A61B 17/7011 606/279 |
| 2008/0255615 A1 | 10/2008 | Vittur et al. | |
| 2008/0269805 A1 | 10/2008 | Dekutoski et al. | |
| 2008/0312694 A1 * | 12/2008 | Peterman | A61B 17/7028 606/257 |
| 2009/0012565 A1 | 1/2009 | Sachs et al. | |
| 2009/0018583 A1 * | 1/2009 | Song | A61B 17/705 606/246 |
| 2009/0048631 A1 * | 2/2009 | Bhatnagar | A61B 17/7004 606/246 |
| 2009/0088799 A1 * | 4/2009 | Yeh | A61B 17/7005 606/246 |
| 2009/0105760 A1 * | 4/2009 | Frey | A61B 17/7026 606/246 |
| 2009/0182378 A1 * | 7/2009 | Choi | A61B 17/7026 606/254 |
| 2009/0187248 A1 | 7/2009 | Dewey et al. | |
| 2009/0292286 A1 | 11/2009 | Carls et al. | |
| 2009/0326582 A1 * | 12/2009 | Songer | A61B 17/702 606/255 |
| 2010/0094302 A1 | 4/2010 | Pool et al. | |
| 2010/0106195 A1 | 4/2010 | Serhan et al. | |
| 2010/0137912 A1 * | 6/2010 | Alcock | A61B 17/7008 606/257 |
| 2010/0174319 A1 * | 7/2010 | Jackson | A61B 17/7008 606/264 |
| 2010/0198261 A1 | 8/2010 | Trieu et al. | |
| 2010/0211104 A1 * | 8/2010 | Moumene | A61B 17/7028 606/257 |
| 2010/0318129 A1 | 12/2010 | Seme et al. | |
| 2011/0009906 A1 * | 1/2011 | Hestad | A61B 17/7005 606/278 |
| 2011/0054408 A1 * | 3/2011 | Wei | A61B 17/68 604/175 |
| 2011/0066188 A1 * | 3/2011 | Seme | A61B 17/7041 606/264 |
| 2011/0130792 A1 * | 6/2011 | Nydegger | A61B 17/7022 606/263 |
| 2011/0270314 A1 | 11/2011 | Mueller et al. | |
| 2012/0071928 A1 * | 3/2012 | Jackson | A61B 17/7005 606/257 |
| 2012/0260923 A1 | 10/2012 | Campagna | |
| 2013/0123851 A1 | 5/2013 | Seme et al. | |
| 2013/0150889 A1 | 6/2013 | Fening et al. | |
| 2014/0074168 A1 | 3/2014 | Mundis et al. | |
| 2014/0296918 A1 | 10/2014 | Fening et al. | |
| 2015/0012045 A1 | 1/2015 | Hestad | |
| 2015/0119939 A1 * | 4/2015 | Frey | A61B 17/7046 606/258 |

(56) References Cited

U.S. PATENT DOCUMENTS

2015/0173820 A1     6/2015    Walker et al.
2015/0230827 A1     8/2015    Zylber et al.
2016/0354118 A1*   12/2016   Belliard ............. A61B 17/7008

OTHER PUBLICATIONS

"European Application Serial No. 10251103.7, Response filed Jun. 21, 2016 to Communication Pursuant to Article 94(3) EPC dated Feb. 11, 2016", 5 pgs.
"U.S. Appl. No. 12/490,845, Final Office Action dated Dec. 21, 2012", 10 pgs.
"U.S. Appl. No. 12/490,845, Non Final Office Action dated Jun. 1, 2011", 13 pgs.
"U.S. Appl. No. 12/490,845, Non Final Office Action dated Dec. 17, 2013", 12 pgs.
"U.S. Appl. No. 12/490,845, Notice of allowance dated Jun. 2, 2014", 10 pgs.
"U.S. Appl. No. 12/490,845, Notice of allowance dated Jul. 1, 2014", 10 pgs.
"U.S. Appl. No. 12/490,845, Response filed Feb. 21, 2012 Final Office Action dated Dec. 21, 2011", 12 pgs.
"U.S. Appl. No. 12/490,845, Response filed Mar. 14, 2014 to Non Final Office Action dated Dec. 17, 2013", 18 pgs.
"U.S. Appl. No. 12/490,845, Response filed Aug. 30, 2011 to Non Final Office Action dated Jun. 1, 2011", 13 pgs.
"U.S. Appl. No. 14/495,297, Non Final Office Action dated Sep. 25, 2015", 12 pgs.
"U.S. Appl. No. 14/495,297, Notice of Allowance dated Jan. 21, 2016", 7 pgs.
"U.S. Appl. No. 14/495,297, Response filed Dec. 17, 2015 to Non Final Office Action dated Sep. 25, 2015", 9 pgs.
"European Application Serial No. 10251103.7, Communication Pursuant to Article 94(3) EPC dated Feb. 11, 2016", 4 pgs.
"European Application Serial No. 10251103.7, Extended European Search Report dated Oct. 19, 2010", 8 pgs.
"European Application Serial No. 10251103.7, Response filed Jun. 27, 2011 to Extended European Search Report dated Oct. 19, 2010", 13 pgs.
Dwyer, A F, et al., "An Anterior Approach to Scoliosis", Clinical Orthopedics and Related Research, No. 62, (Jan.-Feb. 1969), 192-202.
ZIMMER INC, "Spinal Instrumentation", Section D, (1987), pp. D38-D42.
"European Application Serial No. 10251103.7, Response filed Feb. 9, 2017 to Communication Pursuant to Article 94(3) EPC dated 09-296", 6 pgs.

* cited by examiner

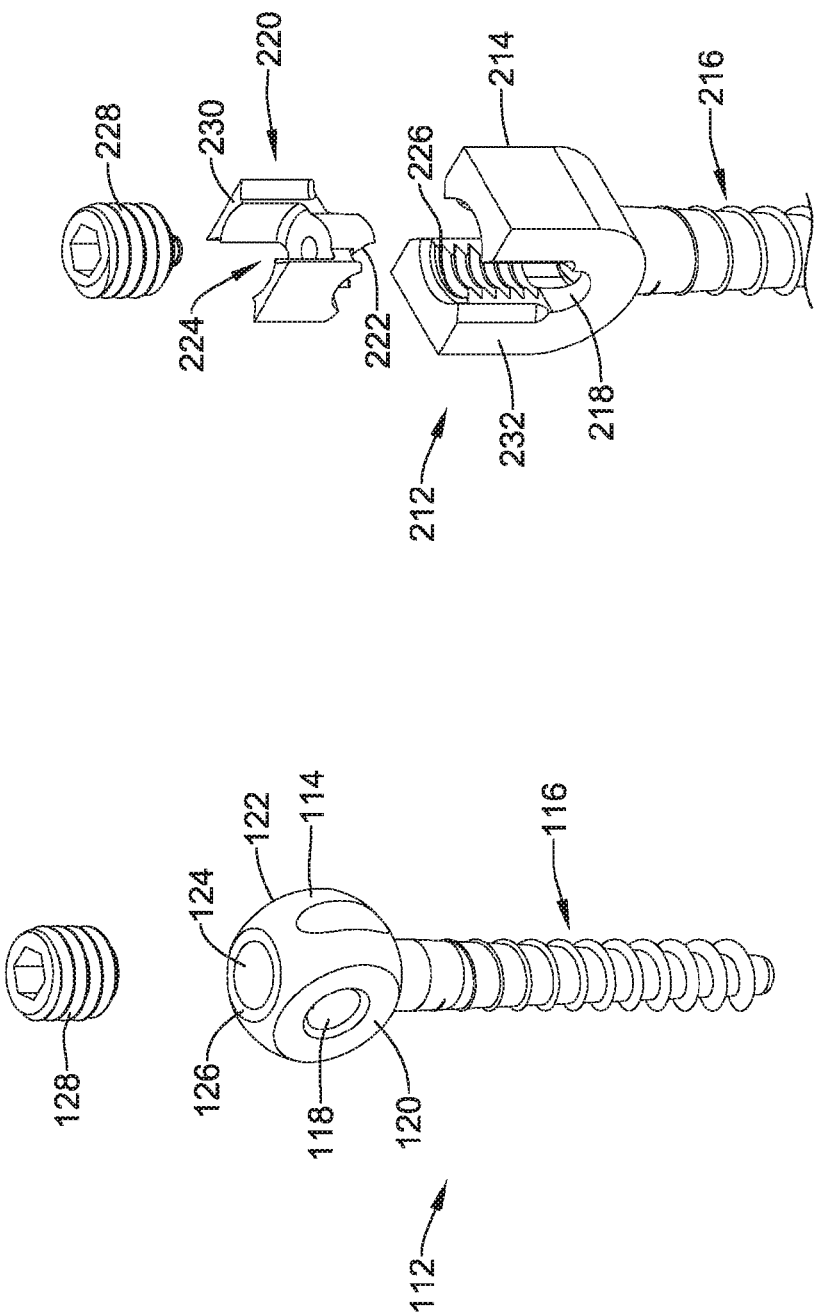

SPINAL CORRECTION TENSIONING SYSTEM

CROSS-REFERENCE TO RELATED APPLICATIONS

This application is a continuation of U.S. patent application Ser. No. 14/495,297, filed Sep. 24, 2014, now issued as U.S. Pat. No. 9,339,299, which is a continuation of U.S. patent application Ser. No. 12/490,845, filed Jun. 24, 2009, now issued as U.S. Pat. No. 8,876,867, the entire contents of which are incorporated herein by reference.

TECHNICAL FIELD

The disclosure is directed to a system, apparatus and method for providing stabilization to one or more vertebrae of a spinal column. More particularly, the disclosure is directed to a system, apparatus and method for correcting a spinal deformity.

BACKGROUND

The spinal column is a highly complex system of bones and connective tissues that provides support for the body and protects the delicate spinal cord and nerves. The spinal column includes a series of vertebrae stacked one on top of the other, each vertebra includes a vertebral body including an inner or central portion of relatively weak cancellous bone and an outer portion of relatively strong cortical bone. An intervertebral disc is situated between each vertebral body to cushion and dampen compressive forces experienced by the spinal column. A vertebral canal, called the foramen, containing the spinal cord and nerves is located posterior to the vertebral bodies. In spite of the complexities, the spine is a highly flexible structure, capable of a high degree of curvature and twist in nearly every direction. For example, the kinematics of the spine normally includes flexion, extension, rotation and lateral bending.

There are many types of spinal column disorders including scoliosis (abnormal curvature and twisting of the spine), kyphosis (abnormal forward curvature of the spine, usually in the thoracic spine), excess lordosis (abnormal backward curvature of the spine, usually in the lumbar spine), spondylolisthesis (forward displacement of one vertebra over another, usually in a lumbar or cervical spine) and other disorders caused by abnormalities, disease, or trauma, such as ruptured or slipped discs, degenerative disc disease, fractured vertebra, and the like. Patients that suffer from such conditions usually experience extreme and debilitating pain as well as diminished range of motion and nerve function. These spinal disorders may also threaten the critical elements of the nervous system housed within the spinal column.

There is an ongoing need to provide alternative systems, apparatuses, and methods of correcting deformities of the spinal column.

SUMMARY

The disclosure is directed to several alternative systems, apparatuses and methods of correcting a spinal deformity.

Accordingly, one illustrative embodiment is a vertebral column correction system including a first vertebral anchor configured to be secured to a first vertebra and a second vertebral anchor configured to be secured to a second vertebra. The vertebral column correction system may further include one or more intermediate vertebral anchors, each configured to be secured to an intermediate vertebra located between the first vertebra and the second vertebra. The vertebral anchors may each have a head portion. A connection member may be configured to extend through the head portion of the first vertebral anchor, through the head portion of each of the one or more intermediate vertebral anchors, and through the head portion of the second vertebral anchor. At least a portion of the connection member may be a flexible member configured for tensioning between at least two vertebral anchors. The connection member may be sized for location within the head portion of each of the one or more intermediate vertebral anchors and may be sized to be longitudinally displaceable through the head portion of at least one of the one or more intermediate vertebral anchors. The vertebral column correction system may be free of structure that constrains the displacement of the head portion of the first vertebral anchor toward the head portion of each of the one or more intermediate vertebral anchors.

Another illustrative embodiment is a vertebral column correction system including a first vertebral anchor and a second vertebral anchor configured to be secured to a first vertbra and a second vertebra, respectively. The vertebral column correction system may further comprise one or more intermediate vertebral anchors, each configured to be secured to an intermediate vertebra located between the first vertebra and the second vertebra. The vertebral anchors may each comprise a head portion. A connection member may be configured to extend through the head portion of the first vertebral anchor, through the head portion of each of the one or more intermediate vertebral anchors, and through the head portion of the second vertebral anchor. At least a portion of the connection member may be a flexible member configured for tensioning between at least two vertebral anchors. The vertebral column correction system may further comprise a tensioning member configured to be coupled to a first end of the connection member and positionable on a side of the head portion of the first vertebral anchor away from the one or more intermediate vertebral anchors and the second vertebral anchor. The tensioning member may be configured to hold the connection member in tension between the first vertebral anchor and the second vertebral anchor.

Yet another illustrative embodiment is a method of correcting a spinal deformity. The method includes securing a first vertebral anchor to a first vertebra, securing a second vertebral anchor to a second vertebra, and securing one or more intermediate vertebral anchors to one or more intermediate vertebra located between the first vertebra and the second vertebra. Each of the vertebral anchors may include a head portion. A connection member may be captured within the head portions of each of the one or more intermediate vertebral anchors while maintaining longitudinal movement of the connection member through the head portions of at least one of the one or more intermediate vertebral anchors. A tensioning member may be coupled to a first end of the connection member. The tensioning member may be positioned on a side of the head portion of the first vertebral anchor away from the one or more intermediate vertebral anchors and the second vertebral anchor. A second end of the connection member may be secured to the head portion of the second vertebral anchor. The connection member may be tensioned to a desired amount of tension.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which:

FIGS. 3A-3D are alternative embodiments of illustrative vertebral anchors which may be used with the vertebral column correction system of FIG. 1;

Figure 1:
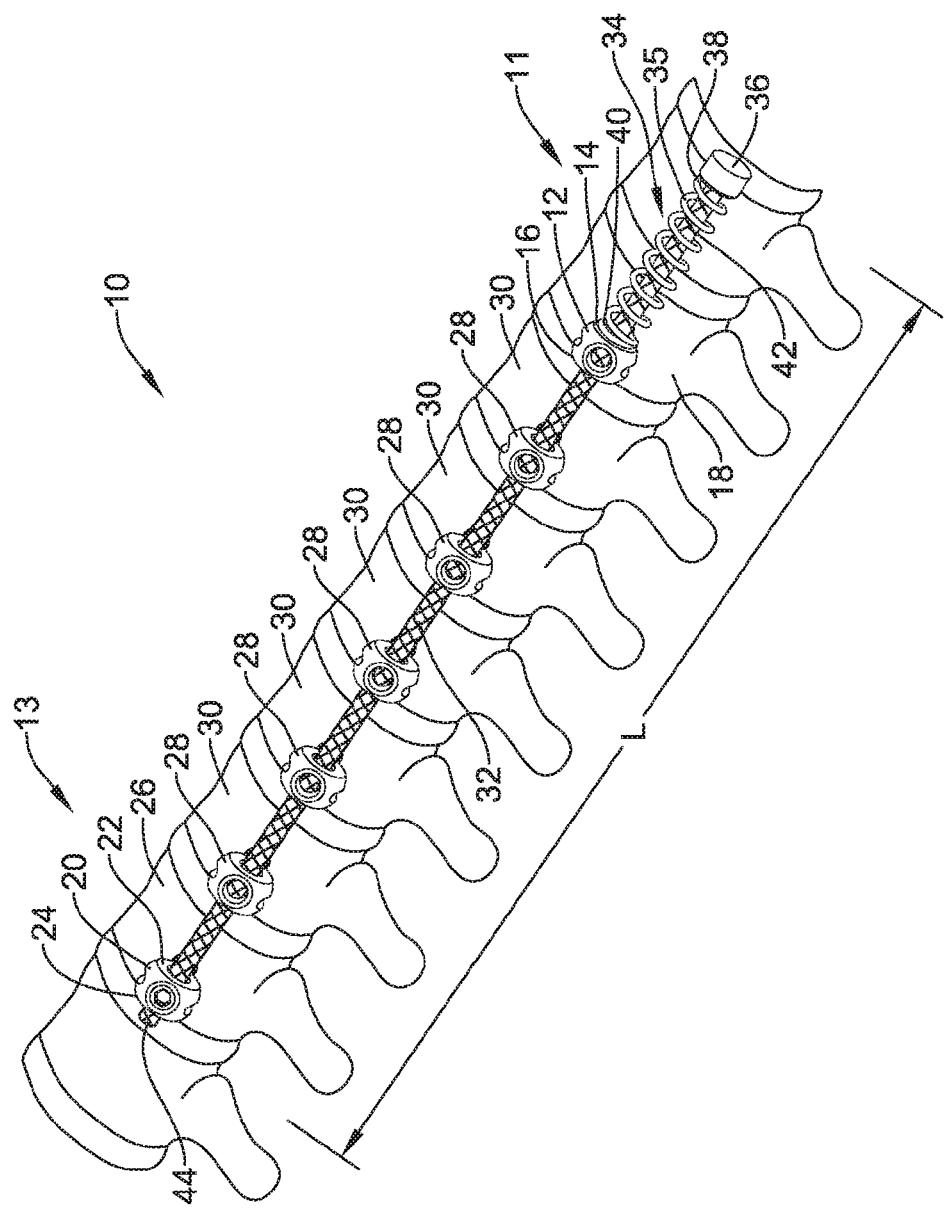
FIG. 1 is a perspective view of an illustrative vertebral column correction system installed along a portion of a spinal column.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Now referring to the drawings, FIG. 1 is a perspective view of an illustrative vertebral column correction system 10. The vertebral column correction system 10 may be used to correct spinal deformities, such as scoliosis, kyphosis, or other deformities with or without fusing one or more joint segments. The vertebral column correction system 10 may have a first end portion 11 and a second end portion 13. In some embodiments, the vertebral column correction system 10 may comprise a first vertebral anchor 12 having a first side surface 14 and a second side surface 16 secured to a first vertebra 18. The vertebral column correction system 10 may further comprise a second vertebral anchor 20 having a first side surface 22 and a second side surface 24 secured to a second vertebra 26. The second vertebra 26 may be adjacent to the first vertebra 18 or may be spaced one, two, three, four, or more vertebrae from the first vertebra 18. The vertebral column correction system 10 may further comprise one or more intermediate vertebral anchors 28 disposed between the first and second vertebral anchors 12, 20. Each of the one or more intermediate vertebral anchors 28 may be secured to one or more vertebra 30 between the first and second vertebrae 18, 26. Each of the vertebral anchors 12, 20, 28 may comprise a head portion and a shank portion, some examples of which will be discussed in more detail with respect to FIGS. 3A-3D.

The vertebral column correction system 10 may further comprise a connection member 32, such as a flexible cord, or other flexible member, extending through the head portion of the first vertebral anchor 12 towards the second vertebral anchor 20. In some embodiments, the connection member 32 may vary in flexibility and elongation properties along the length L of the connection member 32. For example, a portion of the connection member 32 may be significantly more rigid if greater correction of a spinal deformity is needed at particular levels of the spine and less rigid in levels of the spine requiring less correction.

The connection member 32 may be held in tension between the first and second vertebral anchors 12, 20. In some embodiments, the vertebral column correction system 10 may further comprise a tensioning member 34, such as a spring member 35, to provide tension to the connection member 32 and potential elongation of the connection member 32. In some embodiments, the tensioning member 34 may be loaded in compression in order to apply tension to the connection member 32. For example, the tensioning member 34 may be a helical spring or a polymeric spacer, such as a polycarbonate urethane (PCU) spacer, for example, which may be loaded in compression. The tensioning member 34 may be disposed over the connection member 32 and between the first side surface 14 of the first vertebral anchor 12 and a ferrule flange 36. The tensioning member 34, shown as a spring member 35, may have a first end 38 adjacent to the ferrule flange 36 and a second end 40 adjacent to the first side surface 14 of the first vertebral anchor 12. The ferrule flange 36 may be attached to a first end 42 of the connection member 32 such that the connection member 32 extends through the tensioning member 34 (e.g., the spring member 35). For instance, the ferrule flange 36 may be crimped, clamped, or otherwise secured to the first end 42.

The vertebral column correction system 10 may be free of any structure that constrains the displacement of the head portion of the first vertebral anchor 12 towards the head portion of each of the intermediate vertebral anchors 28. Similarly, the vertebral column correction system 10 may be free of any structure that constrains the displacement of the head portion of the second vertebral anchor 20 towards the head portion of each of the intermediate vertebral anchors 28. In some embodiments, the vertebral column correction system 10 may also be free of any structure that constrains the displacement of the head portion of the intermediate vertebral anchors 28 toward one another. For instance, the vertebral column correction system 10 may not include spacers or other structure disposed around the connection member 32 between the head portion of adjacent vertebral anchors 12, 20, 28.

Figure 2:
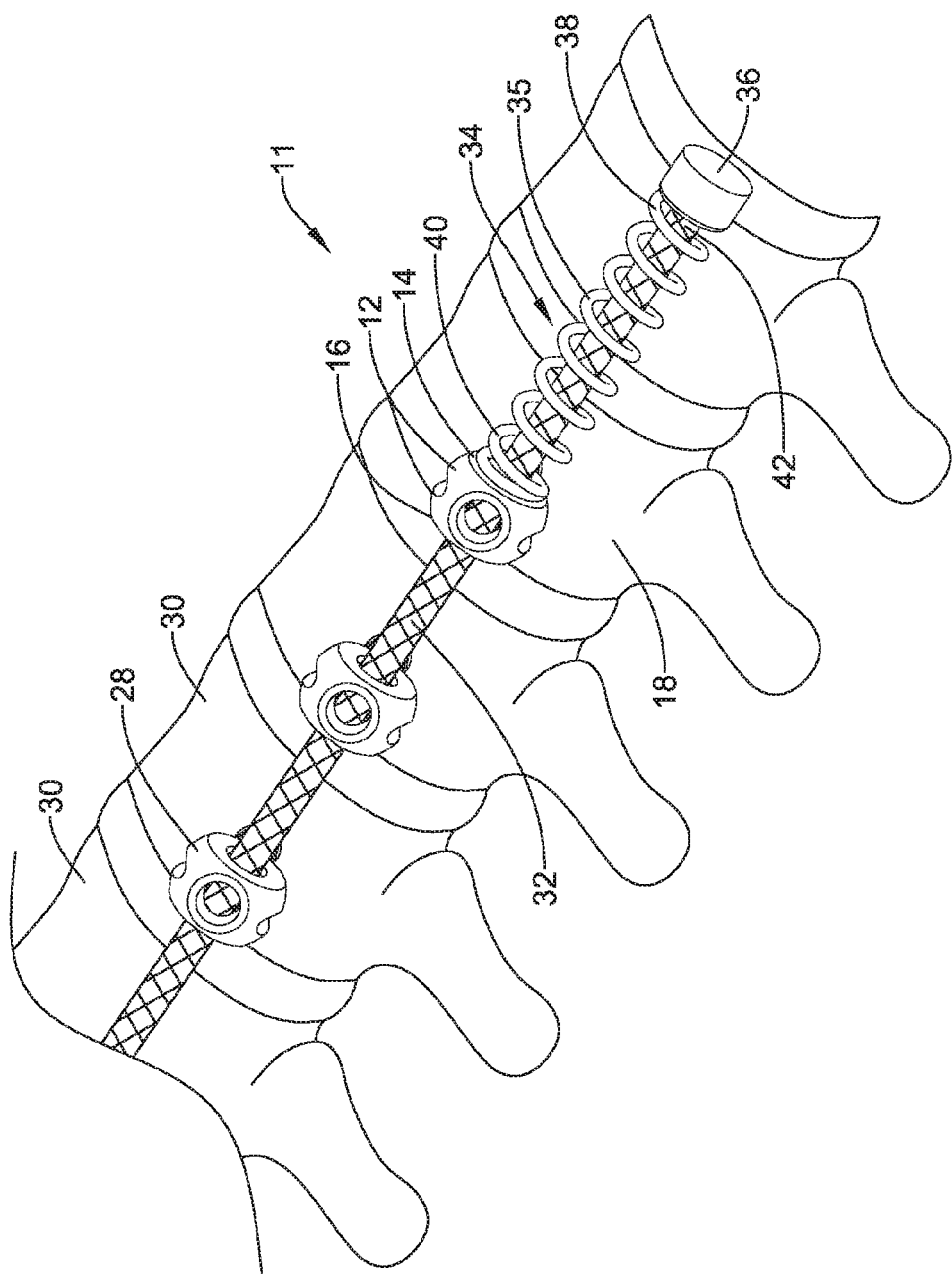
FIG. 2 is a perspective view illustrating the first end portion of the illustrative vertebral column correction system of FIG. 1.

Turning now to FIG. 2, which illustrates a perspective view of the first end portion 11 of the illustrative vertebral column correction system 10, the tensioning member 34, connection member 32, and ferrule flange 36 will be discussed in more detail. The connection member 32 may have a first end 42 and a second end 44 (see FIG. 1). While the connection member 32 is shown having a circular cross-section, the connection member 32 may have any cross-section desired such as, but not limited to, square, rectangle, polygonal, or elliptical. In one embodiment, the connection member 32 may be formed from polyethylene-terephthalate (PET), although it will be recognized that various other materials suitable for implantation within the human body and for providing stabilization of the spine while maintaining flexibility may be used. In other embodiments, the connection member 32 can be constructed of other flexible materials such as metal, polymeric materials, or combinations of flexible materials. The connection member 32 may be of any length necessary to extend between two, three, four, or more vertebrae of the spinal column.

A ferrule flange 36 may be fixedly attached to a first end 42 of the connection member 32. The ferrule flange 36 may be attached adhesively, mechanically (e.g. clamped or crimped), or by any other method known in the art. In some instances, the tensioning member 34 may be placed over the flexible cord 32 by sliding the tensioning member 34 over the second end 44 of the cord 32 and advancing the tensioning member 34 towards the ferrule flange 36, attached to the first end 42 of the connection member 32, such that the connection member 32 extends through the tensioning member 34. In some embodiments, the vertebral column correction system 10 may further include a flange (not explicitly shown) disposed between the tensioning member 34 and the first side surface 14 of the first vertebral anchor 12.

The tensioning member 34 (e.g., the spring member 35) may allow the connection member 32 to be placed under various amounts of tension depending on the amount of compression placed on the tensioning member 34 (e.g., the spring member 35). In some embodiments, the spring member 35, or other tensioning member, may allow the vertebral column correction system 10 to be tensioned and allow movement in all directions while providing tension to the connection member 32. The spring member 35, or other tensioning member, may also allow tension and travel to be customized by a surgeon to provide the intended spinal correction by controlling the compression of the spring member 35, or other tensioning member, and/or adjusting the compression of the spring member 35, or other tensioning member, intra-operatively and/or post-operatively.

In some embodiments, the ferrule flange 36 may prevent the tensioning member 34 from advancing past the first end 42 of the connection member 32. Once the tensioning member 34 is in place, the second end 44 of the connection member 32 may be advanced longitudinally through the head portion of the vertebral anchors 12, 20, 28, beginning with the first vertebral anchor 12, continuing with the intermediate vertebral anchor(s) 28, then the second vertebral anchor 20. Thus, the connection member 32 may be advanced through the head portion of each intermediate vertebral anchor 28 prior to being advanced through the head of the second vertebral anchor 20. In embodiments in which the vertebral anchors are top loading pedicle screws, the system 10 may be positioned in the head portions in another order if desired. For instance, in embodiments in which at least the intermediate vertebral anchors 28 are top-loaded pedicle screws, the connection member 32 may be advanced through the intermediate vertebral anchors 28 prior to or subsequent to positioning the connection member 32 in the head portions of the first and/or second vertebral anchors 12, 20.

Figure 3D:
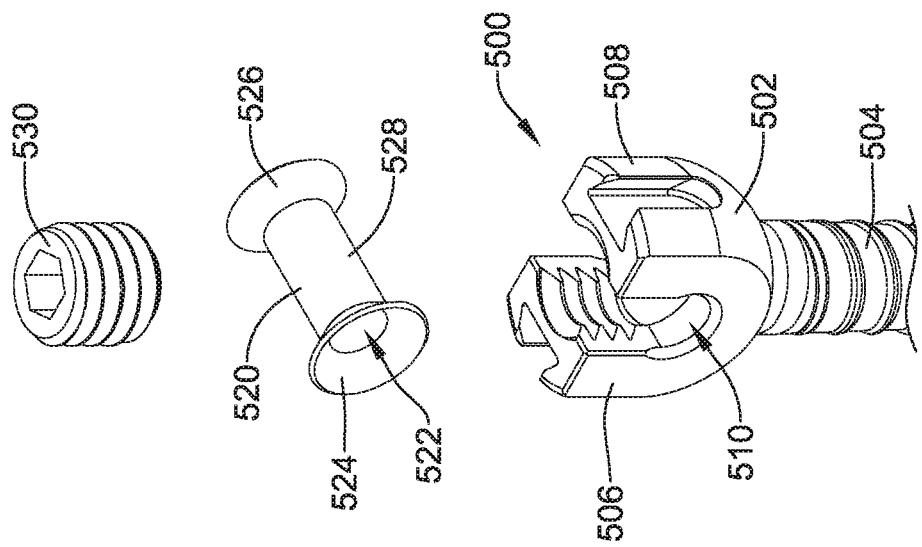

FIGS. 3A-3D illustrate alternative embodiments of an illustrative vertebral anchor which may be used with the vertebral column correction system 10. FIG. 3A illustrates a vertebral anchor 112 having a head portion 114 and a shank portion 116. While the shank portion 116 is shown as a threaded shank, it is contemplated that the vertebral anchor 112 may comprise other devices for securing to a vertebra (e.g. vertebral hooks). In some embodiments, the head portion 114 may have a generally circular cross-sectional shape. In other embodiments, the head portion 114 may comprise a cross-sectional shape other than circular such as, but not limited to, generally square, rectangular, polygonal, and elliptical. The head portion 114 may further include a channel, such as a through hole or bore 118, extending from a first side surface 120 to a second side surface 122 for receiving the connection member 32. The through hole 118 or other channel may be sized and shaped to accommodate the connection member 32. In some embodiments, the through hole 118 may have a diameter that is substantially the same as an outer diameter of the connection member 32. In other embodiments, the through hole 118 may have a diameter that is slightly larger or substantially larger than the diameter of the connection member 32. The head portion 114 may further include an opening, such as a bore 124, extending from a top surface 126 of the head portion 114 to the through hole 118. The bore 124 may comprise a threaded region (not explicitly shown) for receiving a set screw 128 or other locking means. In some embodiments, the set screw 128 may threadably engage the head portion 114 and secure the connection member 32 within the through hole 118. In other embodiments, the connection member 32 may pass through the through hole 118 to capture the connection member 32 in the head portion 114, but may not be secured within the through hole 118 or other channel.

FIG. 3B illustrates an exploded view of another illustrative vertebral anchor 212 having a head portion 214 and a shank portion 216. While the shank portion 216 is shown as a threaded shank, it is contemplated that the vertebral anchor 212 may comprise other devices for securing to a vertebra (e.g. vertebral hooks). The head portion 214 may be generally U-shaped forming a generally concave channel 218 extending from a first side surface 232 to a second side surface. While the channel 218 is shown as generally concave, it is contemplated that the channel 218 may be shaped to conform to the connection member 32. The vertebral anchor 212 may further comprise a locking member 220. The locking member 220 may comprise a generally convex portion 222 configured to mate with the connection member 32. While the locking member 220 is shown as having generally convex portion 222, it is contemplated that the portion 222 may be shaped to generally coincide with the shape of the connection member 32. The locking member 220 may further comprise a bore 224 extending from a top surface 230 towards the generally convex portion 222. The bore 224 may be configured to receive a set screw 228 or other locking means. The head portion 214 of the vertebral anchor 212 may further comprise a threaded region 226 for receiving the set screw 228. When the vertebral anchor 214 is assembled the connection member 32 may be disposed between the channel 218 and the generally convex portion 222 of the locking member 220. The locking member 220 may be held within the head portion 214 of the vertebral anchor 212 by the set screw 228 thus capturing the connection member 32 in the head portion 214. In some embodiments, the set screw 228 may retain the locking member 220 within the head portion 214 of the vertebral anchor 212 without applying a clamping force onto the connection member 32 thus providing a channel which captures the connection member 32 yet allows longitudinal movement of the connection member 32 therethrough. In other embodiments, the set screw 228 may secure the locking member 220 tightly against the connection member 32 such that the connection member 32 is fixedly held within the head portion 214 of the vertebral anchor 212.

Figure 3C:
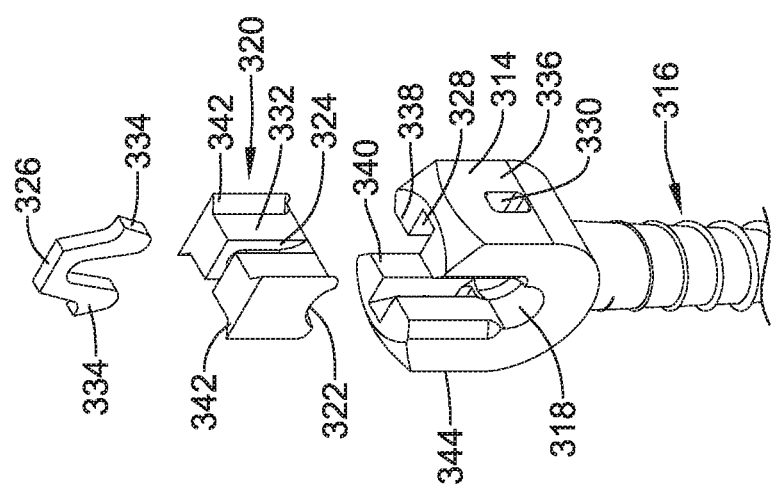

FIG. 3C illustrates an exploded view of another illustrative vertebral anchor 312 having a head portion 314 and a shank portion 316. While the shank portion 316 is shown as a threaded shank, it is contemplated that the vertebral anchor 312 may comprise other devices for securing to a vertebra (e.g. vertebral hooks). The head portion 314 may be generally U-shaped forming a generally concave channel 318. While the channel 318 is shown as generally concave, it is contemplated that the channel 318 may be shaped to conform to the connection member 32. The vertebral anchor 312 may further comprise a locking member 320. The locking member 320 may comprise a generally convex portion 322 configured to mate with the connection member 32. While the locking member 320 is shown as having a generally convex portion 322, it is contemplated that the portion 322 may be shaped to generally coincide with the shape of the connection member 32. The locking member 320 may further comprise a channel 324 extending down a first side 332 and an opposite second side (not explicitly shown) of the locking member 320. The channel 324 may be configured to receive an engaging member 326 or other locking means. The engaging member 326 may further comprise two flared portions 334 configured to mate with holes 330 in the head portion 314 of the vertebral anchor 312.

The head portion 314 of the vertebral anchor 312 may further comprise a slot 328 disposed within the interior portion 338, 340 of the head portion 314 for receiving the engaging member 326. In some embodiments, the slot 328 may be sized such that the engaging member 326 may be under compression while it is disposed within the slot 328. In other embodiments, the slot 328 may be sized such that the engaging member 326 freely slides within the slot 328. The head portion 314 may further comprise a first hole 330, extending from a side portion 336 orthogonal to the channel 318 and into the channel 318. The head portion 314 may comprise a second hole (not explicitly shown) positioned opposite the first hole 330 and extending through a second side portion 344 into the channel 318. The connection member 32 may be placed within the channel 318 prior to assembling the vertebral anchor 312 and the locking member 320. Once the connection member 32 is disposed within the channel 318, the locking member 320 may be placed within the head portion 314 of the vertebral anchor 312. When assembled, the channel 324 of the locking member 320 may coincide with the channel 328 of the head portion 314. The locking member 320 may further comprise flared regions 342 configured to prevent the locking member 320 from being longitudinally displaced from the head portion 314. Once the locking member 320 is disposed within the head portion 314, the engaging member 326 may be advanced through the channels 324, 328 until the flared portions 334 engage the holes 330. When the flared portions 334 engage the holes 330, the locking member 320 may be secured within the head portion 314. When the vertebral anchor 312 is assembled the connection member 32 may be disposed between the channel 318 and the generally convex portion 322 of the locking member 320. The locking member 320 may be held within the head portion 314 of the vertebral anchor 312 by the engaging member 326 thus capturing the connection member 32 in the head portion 314. In some embodiments, the engaging member 326 may retain the locking member 320 within in the head portion 314 of the vertebral anchor 312 without applying a clamping force onto the connection member 32, thus providing a channel which captures the connection member 32. In other embodiments, the engaging member 326 may secure the locking member 320 tightly against the connection member 32 such that the connection member 32 is fixedly held within the head portion 314 of the vertebral anchor 312.

FIG. 3D illustrates an exploded view of another illustrative vertebral anchor 500 having a head portion 502 and a shank portion 504. While the shank portion 504 is shown as a threaded shank, it is contemplated that the vertebral anchor 500 may comprise other devices for securing to a vertebra (e.g., vertebral hooks). The head portion 502 may be generally U-shaped having a first arm 506 and a second arm 508 extending from a base portion of the head portion 502, defining a generally U-shaped concave channel 510 therebetween extending from one side of the head portion 502 to an opposite side of the head portion 502. While the channel 510 is shown as being generally concave, it is contemplated that the channel 510 may be shaped to conform to the connection member 32.

The vertebral anchor 500 may further include a securing member, such as a threaded set screw 530. The set screw 530 may be configured to threadedly engage with threaded portions of the first and second arms 506, 508 of the head portion 502. In other embodiments, the securing member may interlock or otherwise engage the first and second arms 506, 508 of the head portion 502 in any other desired fashion in order to capture a component in the channel 510 of the head portion 502.

A bushing 520 may be configured to be disposed in the channel 510 of the head portion 502. The bushing 520 may include a first flared end 524, a second flared end 526 and a medial portion 528 between the first flared end 524 and the second flared end 526. The bushing 520 may include a central aperture 522 extending through the bushing 520 from the first flared end 524 to the second flared end 526. The bushing 520 may be configured such that the medial portion 528 is positionable in the channel 510 of the head portion 502 while the first flared end 524 is located exterior of the head portion 502 and facing a first side of the head portion 502 and the second flared end 526 is located exterior of the head portion 502 and facing a second side of the head portion 502 opposite the first side.

The bushing 520 may be configured such that the connection member 32 may extend through the aperture 522, allowing longitudinal displacement of the connection member 32 through the bushing 420. Thus, when the bushing 520 is secured in the head portion 502 of the vertebral anchor 500 with the set screw 530 or other securing member, the connection member 42 (which passes through the aperture 522) may be captured in the channel 510 of the head portion

502, yet not be fixedly secured to the head portion 502 of the vertebral anchor 500. This configuration may allow the connection member 32 to be longitudinally displaceable through the head portion 502.

Figure 4:
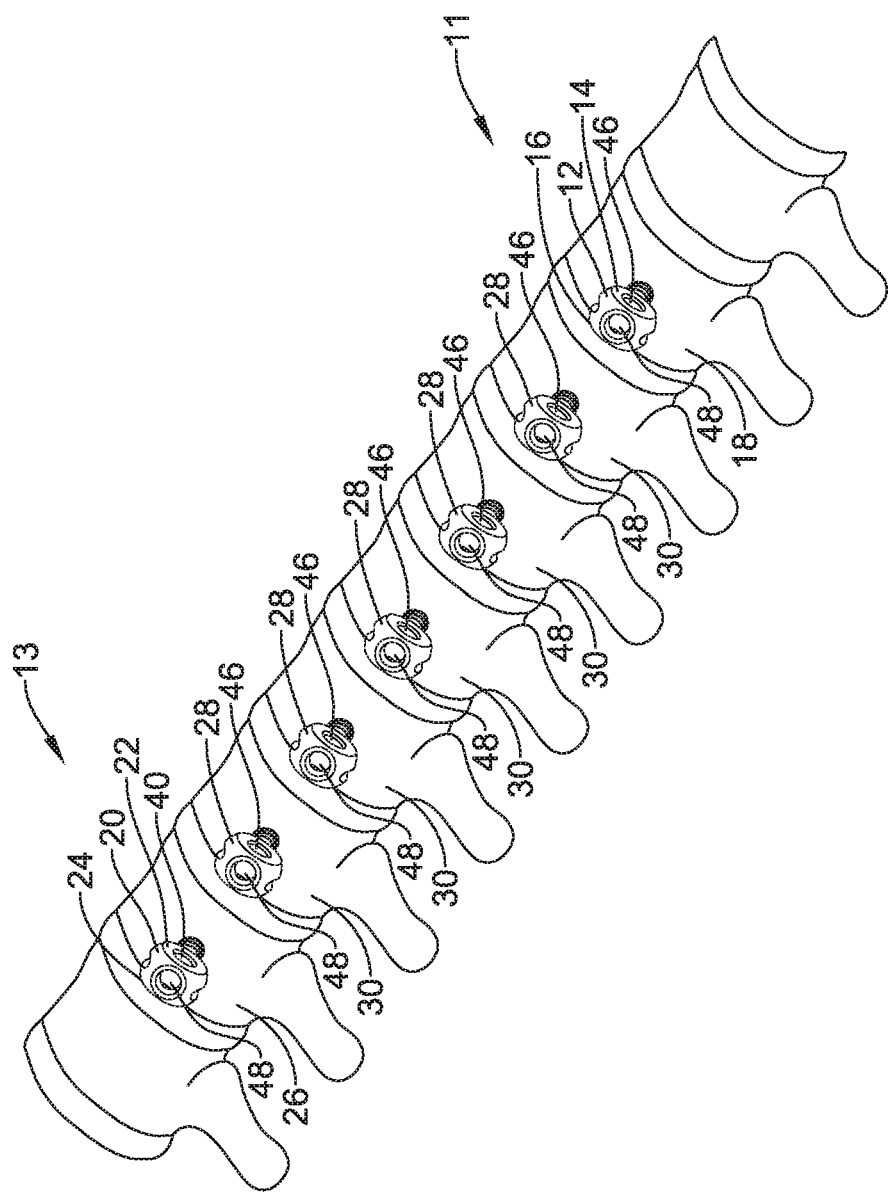
FIGS. 4-7 illustrate one mode of installation of the vertebral column correction system of FIG. 1.

Turning now to FIGS. 4-7, a method for installing the vertebral column correction system 10 along a portion of a spinal column will now be described. Referring to FIG. 4, a first vertebral anchor 12 can be secured to a first vertebra 18. The first vertebral anchor 12 may have a first side surface 14 and a second side surface 16. A second vertebral anchor 20 can be secured to a second vertebra 26. The second vertebral anchor 20 may have a first side surface 22 and a second side surface 24. The second vertebra 26 may be positioned adjacent to the first vertebra 18 or may be spaced one, two, three, four, or more vertebrae from the first vertebra 18. In some embodiments, the vertebral column correction system 10 may further comprise one or more intermediate vertebral anchors 28 disposed between the first and second vertebral anchors 12, 20. The one or more intermediate vertebral anchors 28 may be secured to one or more vertebrae 30 between the first and second vertebrae 18, 26. The vertebral anchors 12, 20, 28 may comprise channels, such as through holes 46 for receiving a connection member 32, such as the pedicle screw illustrated in FIG. 3A. In some embodiments, one or more of the vertebral anchors 12, 20, 28 may be top loading pedicle screws having a U-shaped channel, such as those illustrated in FIGS. 3B-3D, for receiving the connection member 32 therethrough. The vertebral anchors 12, 20, 28 may further comprise a bore 48, or other opening, extending from a top surface of the vertebral anchors 12, 20, 28 for receiving a set screw or other locking means 50. Vertebral anchors, such as those illustrated in FIGS. 3B-3D may include a mechanism to provisionally hold the connection member 32 within the channel as a multi-level construct is assembled.

Figure 5:
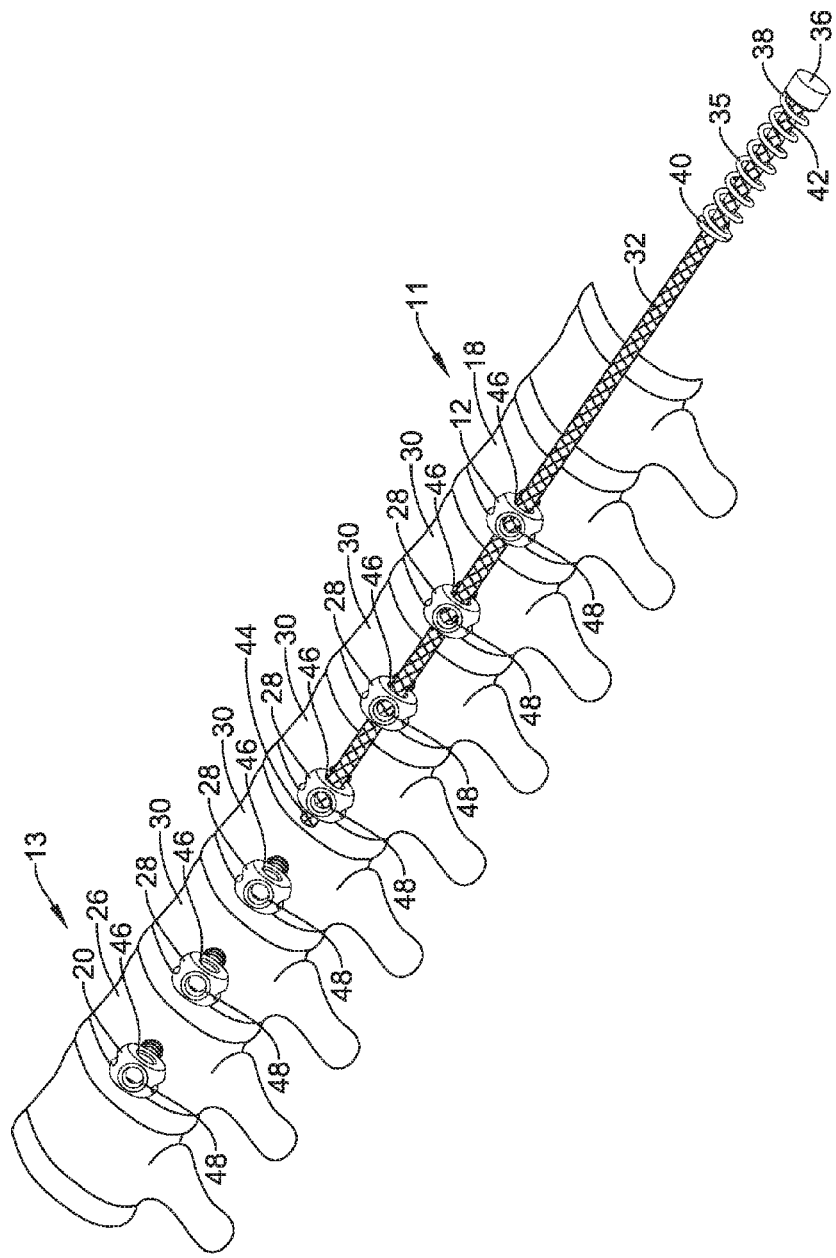
Figure 6:
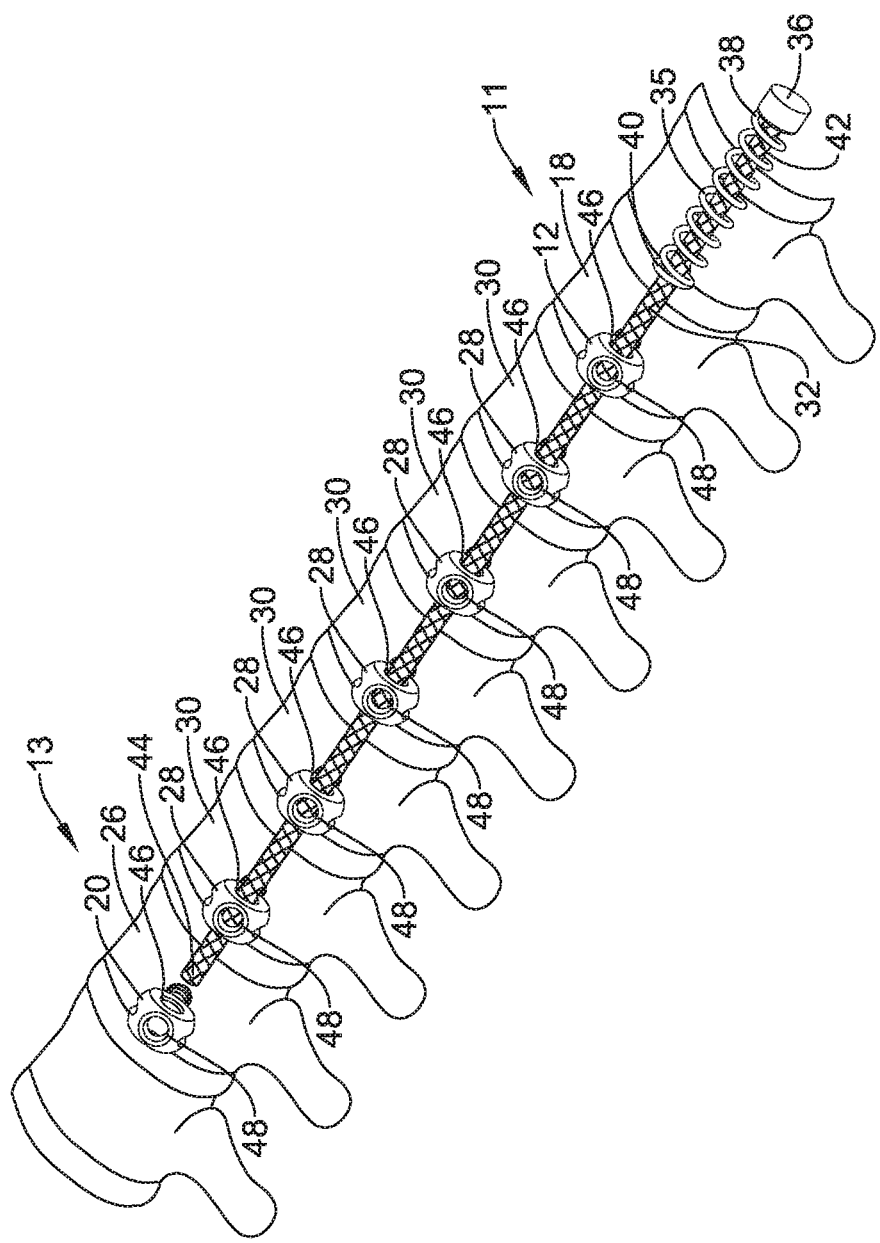

Referring now to FIGS. 5-6, once the vertebral anchors 12, 20, 28 are secured in the vertebrae 18, 26, 30, the connection member 32 may be advanced longitudinally through the channels, such as through holes 46, of the vertebral anchors 12, 20, 28. In some embodiments, the ferrule flange 36 may be attached to the first end 42 of the connection member 32 prior to advancing the connection member 32 through the through holes 46, or other channels. In this embodiment, the tensioning member 34, shown as the spring member 35, may be disposed over the connection member 32 prior to advancing the connection member 32 through the through holes 46, or other channels. In some embodiments, the ferrule flange 16 may be secured to the connection member 32 prior to the placement of the tensioning member 34 (e.g., the spring member 35) and the tensioning member 34 may be placed over the second end 44 of the connection member 32 and advanced towards the first end 42 of the connection member 32 and the ferrule flange 36.

In other embodiments, the tensioning member 34 may be disposed over the connection member 32 prior to securing the ferrule flange 36 to the first end 42 of the connection member 32. In this particular embodiment, the tensioning member 34 may be advanced over either end 42, 44 of the connection member 32 and positioned adjacent the first end 42 prior to advancing the connection member 32 through the through holes 46, or other channels.

In other embodiments, the connection member 32 may be advanced through some of the vertebral anchors 12, 20, 28 or all of the vertebral anchors 12, 20, 28 prior to disposing the tensioning member 34 over the connection member 32. In this particular embodiment, the second end 44 of the connection member 32 may be advanced through any number of vertebral anchors 12, 20, 28 and the tensioning member 34 may be placed over the first end 42 of the connection member 32. The ferrule flange 36 may then be secured to the first end 42 of the connection member 32 after the tensioning member 34 has been positioned. The second end 44 of the connection member 32 may be advanced through the through hole 46, or other channel, of the first vertebral anchor 12 and then longitudinally advanced through the through hole 46, or other channel, of each intermediate vertebral anchor 28 towards the second vertebral anchor 20.

Figure 7:
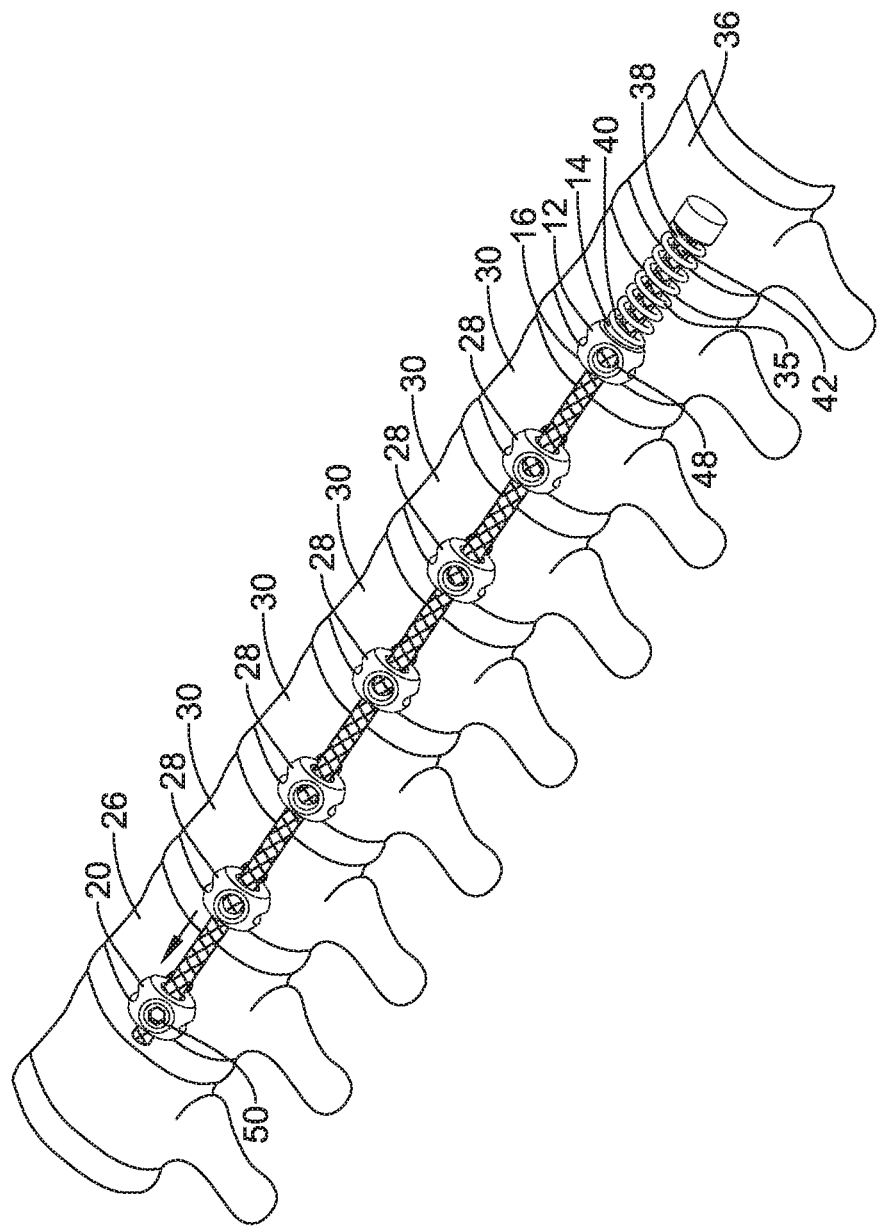

Referring now to FIG. 7, once the second end 44 of the connection member 32 is advanced through the through hole 46, or other channel, of the second vertebral anchor 20, tension may be placed on the connection member 32 by further pulling the connection member 32 in the direction the arrow in FIG. 7 away from the spring member 35, or other tensioning member. As can be seen in FIG. 7, the spring member 35 has a first end 38 abutting the ferrule flange 36 and a second end 40 abutting the first side 14 of the first vertebral anchor 12. As the connection member 32 is tensioned, the spring member 35, or other tensioning member, may be compressed and thus shortened from a first length to a shorter second length, putting the spring member 35, or other tensioning member, in compression. In some embodiments, the spring member 35 may be a helical coil. The coil windings of a helical coil may become closer together when the spring member 35 is under compression. The tensioning of the connection member 32 may be done with or without a tensioning tower or other tensioning instrument. The connection member 32 may be tensioned to a prescribed tension and/or adequate correction of the deformity. The compression in the tensioning member 34 may maintain a desired amount of tension in the connection member 32. Once the proper amount of tension is placed on the connection member 32, a set screw 50, or other locking means, may be placed in the bore 48, or other opening, of the second vertebral anchor 20 to fixedly secure the second end 44 of the connection member 32 to the head portion of the second vertebral anchor 20. The intermediate vertebral anchors 28 may or may not have a set screw 50, or other locking means to secure the connection member 32 to the vertebral anchor. Based on the treatment required, set screws 50 or other locking means may be used to secure the connection member 32 with one or more of the intermediate vertebral anchors 28. In embodiments that do not use a set screw 50 or other locking means at one or more of the intermediate vertebral anchors 28, this may allow for longitudinal displacement of the connection member 32 through the head portion of the intermediate vertebral anchors 28 while the connection member 32 is captured in the head portions of the intermediate vertebral anchors 28.

In some embodiments, one or more of the intermediate vertebral anchors 28 may be one of the vertebral anchors shown in FIGS. 3B-3D, which capture the connection member 32 in the head portions without fixedly securing the connection member 32 to the head portions. However, in some embodiments, a set screw 50 may be used to secure the connection member 32 at an intermediate vertebral anchor 28, if desired. It is contemplated that the connection member 32 may be secured at any one or more of the vertebral anchors 12, 20, 28. The set screw 50 may lock the connection member 32 in place and help maintain the proper amount of tension. If there is excess length of connection member 32 present, the connection member 32 may be trimmed before or after tensioning. The tension on the connection member 32 by the spring member 35 or other tensioning member, may be further adjustable by a screw mechanism or other tension adjustment mechanism to attain a desired amount of tension in the connection member 32. In some embodiments, compression of the tensioning member 34 (e.g., the spring member 35), and thus tension of the connection member 32 may be adjusted post operatively and/or percutaneously to maintain and/or adjust the tension of the connection member 32. The tension in the connection member 32 may provide a corrective force to the spinal column to correct a deformity to the spinal column.

Figure 8:
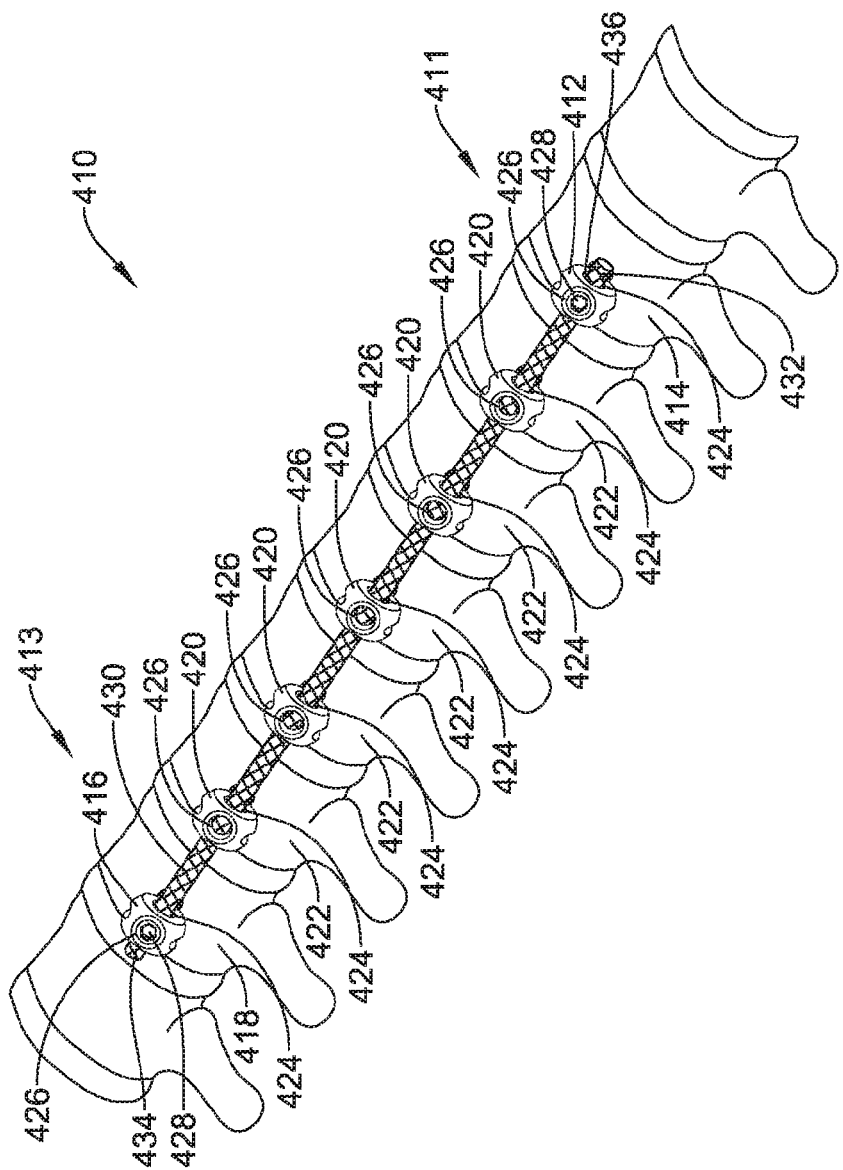
FIG. 8 is an alternative embodiment of an illustrative vertebral column correction system installed along a portion of a spinal column under tension.

Referring now to FIG. 8, an alternative embodiment of a vertebral column correction system 410 will now be described. The vertebral column correction system 410 may have a first end portion 411 and a second end portion 413. The vertebral column correction system 410 may comprise a first vertebral anchor 412 secured to a first vertebra 414. A second vertebral anchor 416 may be secured to second vertebra 418. In some embodiments, the second vertebra 418 may be positioned adjacent to the first vertebra 414 or in other embodiments, it may be spaced one, two, three, four, or more vertebrae from the first vertebra 414. In some embodiments, the vertebral column correction system 410 may further comprise one or more intermediate vertebral anchors 420 disposed between the first and second vertebral anchors 412, 416. Each of the one or more intermediate vertebral anchors 420 may each be secured to a vertebra 422 between the first and second vertebrae 414, 418. The vertebral anchors 412, 416, 420 may comprise channels, such as through holes 424, for receiving a connection member 430 (e.g., a flexible cord or other flexible member) such as the pedicle screw illustrated in FIG. 3A. In some embodiments, one or more of the vertebral anchors 412, 416, 420 may be top loading pedicle screws having a U-shaped channel, such as those illustrated in FIGS. 3B-3D, for receiving the connection member 430 therethrough. The vertebral anchors 412, 416, 420 may further comprise a bore 426, or other opening, extending from a top surface of the vertebral anchors 412, 416, 420 for receiving a set screw or other locking means 428.

The vertebral column correction system 410 may be free of any structure that constrains the displacement of the head portion of the first vertebral anchor 412 towards the head portion of each of the intermediate vertebral anchors 420. Similarly, the vertebral column correction system 410 may be free of any structure that constrains the displacement of the head portion of the second vertebral anchor 416 towards the head portion of each of the intermediate vertebral anchors 420. In some embodiments, the vertebral column correction system 410 may also be free of any structure that constrains the displacement of the head portion of the intermediate vertebral anchors 420 toward one another. For instance, the vertebral column correct on 410 may not include spacers or other structure disposed around the connection member 430 between the head portion of adjacent vertebral anchors 412, 416, 420.

Once the vertebral anchors 412, 416, 420 are secured to the vertebrae 414, 418, 422, the connection member 430, such as a flexible cord or other flexible member, may be advanced through the channels, such as the through holes 424, of the vertebral anchors 412, 416, 420. A first end 432 of connection member 430 may be positioned within the channel or through hole 424 of the first vertebral anchor 412. A set screw 428, or other locking means, may be positioned within the bore 426 of the first vertebral anchor 412 to fixedly secure the connection member 430 to the head portion of the first vertebral anchor 412. A second end 434 of the connection member 430 may be longitudinally advanced through the channel or through hole 424 of each intermediate vertebral anchor 420 towards the second vertebral anchor 416. The second end 434 of the connection member 430 may be advanced through the channel or through hole 424 of the second vertebral anchor 416. With the connection member 430 secured at the first end portion 411 of the vertebral column correction system 410, tension may be placed on the connection member 430 from the second end 413 of the vertebral column correction system 410. The tensioning of the connection member 430 may be done with or without tensioning tower or other tensioning instrument. The connection member 430 may be tensioned to a prescribed tension and/or adequate correction of the deformity. Once the proper amount of tension is placed on the connection member 430, a set screw 428, or other locking means, may be placed in the bore 426 of the second vertebral anchor 416, fixedly securing the connection member 430 to the head portion of the second vertebral anchor 416. The connection member 430 may be captured in the head portion of the intermediate vertebral anchors 420 yet not be fixedly secured thereto, which may allow for longitudinal displacement of the connection member 430 through the head portion of the intermediate vertebral anchor(s) 420. However, in some embodiments, a set screw 426, or other locking means, may be used to secure the connection member 430 at an intermediate vertebral anchor 420. It is contemplated that the connection member 430 may be secured at any one or more of the vertebral anchors 412, 416, 420. The set screw 428 may lock the connection member 430 in place and help maintain the proper amount of tension. If there is excess length of the connection member 430 present at the second end 413 of the vertebral column correction system 10, the connection member 430 may be trimmed before or after tensioning.

The placement of the vertebral column correction systems disclosed herein may depend on the type of deformity to be corrected and/or the curvature of the spinal column to be corrected. The vertebral column correction systems described herein may be particularly advantageous for correcting abnormal curvatures caused by scoliosis. The vertebral column correction systems, through the tension of the connecting member, may exert a restoring force on the vertebrae to move the vertebrae into or toward alignment along the sagittal plane, for example.

Generally, the vertebral column correction system may be secured to the convex side of a curvature of the spinal column in order to realign the spinal column to a straighter or less curved condition by applying a restoring force to the convex side of the abnormal curvature. The vertebral column correction system may be implanted anteriorly, posteriorly, anterolaterally, posterolaterally, or laterally, such that the vertebral column correction system may be secured to an anterior, posterior, anterolateral, posterolateral and/or lateral aspect of vertebrae of the spinal column.

The position of the vertebral anchors and/or other components of the vertebral column correction systems may be dictated by the curvature of the spinal column on a case by case basis. In some instances, the location of the vertebral column correction system may vary from one vertebra to the next vertebra. For example, the position of a vertebral anchor secured to a first vertebra may be different from the position of a vertebral anchor secured to a second vertebra. Thus, in some instances, the vertebral column correction system may be implanted in a fluctuating arrangement from one vertebra to adjacent vertebra of a spinal column. Thus, the vertebral column correction system may follow the outermost aspect of curvature of the spinal column. In instances in which the spinal column has a compound curvature (e.g., has multiple curved portions), it may be desirable to install the vertebral column correction system on the convex sides of each of the curved portions of the spinal column.

A single vertebral column correction system may be installed on the spinal column, or multiple vertebral column correction systems may be installed on the spinal column, depending on the spinal deformity and/or correction desired. For instance, multiple vertebral column correction systems, or components thereof, may be installed in parallel on a single aspect of the spinal column and/or multiple vertebral column correction systems, or components thereof, may be installed at different locations of the spinal column (e.g. throughout different curved regions of the spine). For instance, a plurality of connection members and/or tensioning members may be used in a vertebral column correction system in order to achieve a desired result. In some instances, a single vertebral column correction system may be installed unilaterally (i.e., on a single side), while in other instances multiple vertebral column correction systems may be installed multi-laterally (i.e., on multiple sides). For instance, a first spinal column correction system may be installed along one side of the spinal column, while a second or additional spinal column correction system may be installed along a second side of the spinal column.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A vertebral column correction system comprising:
    a first vertebral anchor including a first head portion and a first shank portion configured to engage bone to secure the first vertebral anchor to a first vertebra;
    a second vertebral anchor including a second head portion and a second shank portion configured to engage bone to secure the second vertebral anchor to a second vertebra;
    a connection member extendable through the first head portion and the second head portion, and sized to be longitudinally displaceable through the first head portion and the second head portion, the connection member configured for tensioning between the first vertebral anchor and the second vertebral anchor;
    a securing element receivable within the second head portion to secure a distal end of the connection member from longitudinal displacement relative to the second head portion; and
    a single tensioning member couplable to a proximal end of the connection member, the tensioning member configured to solely maintain the connection member in tension between the first vertebral anchor and the second vertebral anchor, when the first vertebral anchor is secured to the first vertebra and the second vertebral anchor is secured to the second vertebra,
    wherein the system is free of additional structure applying tension to the connection member between the first vertebral anchor and the second vertebral anchor.

2. The vertebral column correction system of claim 1, wherein the connection member is comprised of one of a flexible material and a rigid material.

3. The vertebral column correction system of claim 1, further comprising an intermediate vertebral anchor including a third head portion and a third shank portion configured to engage bone to secure the intermediate vertebral anchor to a third vertebra in between the first and second vertebrae.

4. The vertebral column correction system of claim 1, wherein the tensioning member is couplable to the proximal end of the connection member adjacent to a side of the first head portion that faces away from the second vertebral anchor so that the tensioning member extends away from the side.

5. The vertebral column correction system of claim 1, wherein the tensioning member comprises a coil spring surrounding the connecting member and restrained from displacement by the first head portion and a ferrule flange connected to the coil spring.

6. The vertebral column correction system of claim 1, wherein the securing member is a set screw and the second head portion comprises an internal threaded portion threadably engageable with the set screw.

7. The vertebral column correction system of claim 6, further comprising a locking member insertable into the threaded portion of the second head portion to capture the connecting member when the set screw forces the locking member to engage the connecting member.

8. The vertebral column correction system of claim 6, further comprising a bushing disposable in the second head portion for receiving the connecting member therethrough, the busing member securable by the set screw.

9. The vertebral column correction system of claim 1, wherein the second head portion further comprises:
    a locking member slidably engageable with a channel of the head portion; and
    an engaging member including a flared portion for lockingly engaging a hole in the second head portion securing the locking member to the second head portion.

10. The vertebral column correction system of claim 1, wherein the system is free of structure that constrains the displacement of the first head portion toward the second head portion.

11. A vertebral column correction system comprising:
    a first vertebral anchor including a first head portion and a first shank portion configured to engage bone to secure the first vertebral anchor to a first vertebra;
    a second vertebral anchor including a second head portion and a second shank portion configured to engage bone to secure the second vertebral anchor to a second vertebra;
    a connection member extendable through the first head portion and the second head portion, and sized to be longitudinally displaceable through the first head portion and the second head portion, the connection member configured for tensioning between the first vertebral anchor and the second vertebral anchor;
    a tensioning member couplable to a first end of the connection member adjacent to a side of the first head portion that faces away from the second vertebral anchor so that the tensioning member extends away from the side, the tensioning member configured to maintain the connection member in tension between the first vertebral anchor and the second vertebral anchor, when the first vertebral anchor is secured to the first vertebra and the second vertebral anchor is secured to the second vertebra;
    a securing member configured to releasably secure a second end of the connection member to the second vertebral anchor; and wherein the system is free of structure between the first vertebral anchor and the second vertebral that applies a tension to the connection member.

12. The vertebral column correction system of claim 11, wherein the connection member is comprised of a flexible material.

13. The vertebral column correction system of claim 11, wherein the connection member is comprised of a rigid material.

14. The vertebral column correction system of claim 11, wherein the tensioning member comprises a coil spring that surrounds the connecting member and restrained from displacement by the first head portion and a ferrule flange connected to the coil spring.

15. The vertebral column correction system of claim 11, wherein the securing member is a set screw and the second head portion comprises an internal threaded portion threadably engageable with the set screw.

16. The vertebral column correction system of claim 15, further comprising a locking member insertable into the threaded portion of the second head portion to capture the connecting member when the set screw forces the locking member to engage the connecting member.

17. The vertebral column correction system of claim 15, further comprising a bushing disposable in the second head portion for receiving the connecting member therethrough, the busing member securable by the set screw.

18. The vertebral column correction system of claim 11, wherein the second head portion further comprises:
a locking member slidably engageable with a channel of the head portion; and
an engaging member including a flared portion for lockingly engaging a hole in the second head portion securing the locking member to the second head portion.

19. The vertebral column correction system of claim 11, wherein the system is free of structure that constrains the displacement of the first head portion toward the second head portion.

* * * * *

UNITED STATES PATENT AND TRADEMARK OFFICE
CERTIFICATE OF CORRECTION

PATENT NO. : 9,770,266 B2
APPLICATION NO. : 15/143962
DATED : September 26, 2017
INVENTOR(S) : Hugh D. Hestad It is certified that error appears in the above-identified patent and that said Letters Patent is hereby corrected as shown below:

On page 3, in Column 2, item (56) References Cited: under "Other Publications", Line 23, delete "09-296"," and insert --Sep. 29, 2016",-- therefor Signed and Sealed this
Twenty-seventh Day of March, 2018

Andrei Iancu
*Director of the United States Patent and Trademark Office*